(12) United States Patent
Moffitt

(10) Patent No.: US 9,327,107 B2
(45) Date of Patent: May 3, 2016

(54) SYSTEM AND METHOD FOR MODELING ELECTRODE MORPHOLOGIES

(75) Inventor: Michael A. Moffitt, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 1121 days.

(21) Appl. No.: 12/904,933

(22) Filed: Oct. 14, 2010

(65) Prior Publication Data

US 2011/0093044 A1 Apr. 21, 2011

Related U.S. Application Data

(60) Provisional application No. 61/252,071, filed on Oct. 15, 2009.

(51) Int. Cl.
*A61N 1/05* (2006.01)
*A61N 1/36* (2006.01)
(52) U.S. Cl.
CPC .............. *A61N 1/05* (2013.01); *A61N 1/36182* (2013.01)
(58) Field of Classification Search
USPC ........................................ 607/115, 116, 148
See application file for complete search history.

(56) References Cited

U.S. PATENT DOCUMENTS

| | | | |
|---|---|---|---|
| 6,516,227 B1 | 2/2003 | Meadows et al. | |
| 6,845,267 B2 | 1/2005 | Harrison et al. | |
| 6,895,280 B2 | 5/2005 | Meadows et al. | |
| 6,950,707 B2 | 9/2005 | Whitehurst | |
| 6,993,384 B2 | 1/2006 | Bradley et al. | |
| 7,346,382 B2 * | 3/2008 | McIntyre et al. | 600/407 |
| 7,650,184 B2 | 1/2010 | Walter | |
| 2006/0017749 A1 * | 1/2006 | McIntyre et al. | 345/664 |
| 2007/0150036 A1 | 6/2007 | Anderson | |
| 2007/0168004 A1 | 7/2007 | Walter | |
| 2007/0168007 A1 | 7/2007 | Kuzma et al. | |
| 2007/0203546 A1 * | 8/2007 | Stone et al. | 607/59 |
| 2008/0004675 A1 * | 1/2008 | King et al. | 607/59 |
| 2008/0183256 A1 * | 7/2008 | Keacher | 607/116 |
| 2011/0093045 A1 | 4/2011 | Moffitt | |

OTHER PUBLICATIONS

PCT International Search Report for PCT/US2010/052748, Applicant: Boston Scientific Neuromodulation Corporation, Form PCT/ISA/210 and 220, dated Jun. 17, 2011 (6 pages).
PCT Written Opinion of the International Search Authority for PCT/US2010/052748, Applicant: Boston Scientific Neuromodulation Corporation, Form PCT/ISA/237, dated Jun. 17, 2011 (8 pages).
PCT Communication Relating to the Results of the Partial International Search Report, Applicant: Boston Scientific Neuromodulation Corporation, Form PCT/ISA/206, dated Mar. 2, 2011 (4 pages).
(Continued)

*Primary Examiner* — Eugene Wu
(74) *Attorney, Agent, or Firm* — Lowe Graham Jones PLLC; Bruce E. Black

(57) ABSTRACT

A system for a neurostimulation device comprises a user input device configured for receiving an electrode morphology having at least one electrode, memory storing at least one basis electrode model, and at least one processor configured for modeling at least one electrode by recalling the at least one basis electrode model from the memory, and using the recalled at least one basis electrode model multiple times to construct a model of the at least one electrode.

20 Claims, 14 Drawing Sheets

(56) References Cited

OTHER PUBLICATIONS

PCT International Preliminary Report on Patentability (Chapter I of the Patent Cooperation Treaty) for PCT/US2010/052748, Applicant: Boston Scientific Scimed, Inc., Form PCT/IB/326 and 373, dated Apr. 26, 2012 (10pages).

File History of U.S. Appl. No. 12/904,967, filed Oct. 14, 2010, Inventor: Michael Moffitt: Notice of Allowance dated Feb. 1, 2012 (16 pages).

* cited by examiner scaling vector
(1 x n)

electrical parameter vector
(1 x n)

mxn
A •

| | |
|---|---|
| 0 | data₁ |
| -0.4 | data₂ |
| 0 | data₃ |
| 0.2 | • |
| 0.8 | • |
| 0 | • |
| -0.6 | • |
| 0 | • |
| • | • |
| • | • |
| • | • |
| 0 | dataₘ |

$$\text{mxn } A \cdot \begin{bmatrix} 0 \\ -0.4 \\ 0 \\ 0.2 \\ 0.8 \\ 0 \\ -0.6 \\ 0 \\ \vdots \\ 0 \end{bmatrix} = \begin{bmatrix} data_1 \\ data_2 \\ data_3 \\ \vdots \\ data_m \end{bmatrix}$$

SYSTEM AND METHOD FOR MODELING ELECTRODE MORPHOLOGIES

RELATED APPLICATION

The present application claims the benefit under 35 U.S.C. §119 to U.S. provisional patent application Ser. No. 61/252,071, filed Oct. 15, 2009. The foregoing application is hereby incorporated by reference into the present application in its entirety.

FIELD OF THE INVENTION

The present invention relates to modeling lead electrodes, and more particularly, to a system and method for modeling lead electrodes for use with an implantable tissue stimulator.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Further, in recent investigations, Peripheral Nerve Stimulation (PNS) systems have demonstrated efficacy in the treatment of chronic pain syndromes and incontinence, and a number of additional applications are currently under investigation.

More pertinent to the present inventions described herein, Deep Brain Stimulation (DBS) has been applied therapeutically for well over a decade for the treatment of neurological disorders. DBS and other related procedures involving implantation of electrical stimulation leads within the brain of a patient are increasingly used to treat disorders, such as Parkinson's disease, dystonia, essential tremor, seizure disorders, obesity, depression, restoration of motor control, and other debilitating diseases via electrical stimulation of one or more target sites, including the ventrolateral thalamus, internal segment of globus pallidus, substantia nigra pars reticulate, subthalamic nucleus (STN), or external segment of globus pallidus. DBS has become a prominent treatment option for many disorders, because it is a safe, reversible alternative to lesioning. For example, DBS is the most frequently performed surgical disorder for the treatment of advanced Parkinson's Disease. There have been approximately 30,000 patients world-wide that have undergone DBS surgery. Consequently, there is a large population of patients who will benefit from advances in DBS treatment options. Further details discussing the treatment of diseases using DBS are disclosed in U.S. Pat. Nos. 6,845,267 and 6,950,707, which are expressly incorporated herein by reference.

During DBS procedures, at least one burr hole is cut through the patient's cranium as not to damage the brain tissue below, a large stereotactic targeting apparatus is mounted to the patient's cranium, and a cannula is scrupulously positioned towards the target site in the brain. Microelectrode recordings may typically be made to determine if a trajectory passes through the desired part of the brain, and if so, the stimulation lead (or leads), which carries an array of electrodes, is then introduced through the cannula, through the burr hole, and along that trajectory into the parenchyma of the brain, such that the electrodes located on the lead are strategically placed at a target site in the brain of the patient.

Typically, an imaging device, such as a magnetic resonant imager (MRI) or a computed tomography (CT) imager may be used to confirm the lead position. Once the lead is properly positioned, the portion of the lead exiting the burr hole is subcutaneously routed underneath the patient's scalp to a neurostimulator implanted in the patient at a site remote from the burr hole (e.g., the patient's chest region). The neurostimulator generates electrical stimulation pulses in accordance with a set of stimulation parameters programmed into the neurostimulator.

Significantly, it is crucial that proper location and maintenance of the lead position be accomplished in order to continuously achieve efficacious therapy. In DBS applications, the target site (or sites) that is intended for electrical stimulation is about the size of a pea and is located deep within the patient's brain. Thus, lead displacements of less than a millimeter may have a deleterious effect on the patient's therapy. Because the stimulation region needs to be in the correct location to achieve optimal therapy and minimization of side-effects, stimulation leads typically carry many electrodes (e.g., four), so that at least one of the electrodes is near the target and allow programming of the electrodes to place the stimulation field in that region of interest. To this end, after the stimulation leads are implanted within the brain of a patient and confirmed to be in the correct position relative to the target region, a fitting procedure is typically performed to select one or more effective sets of stimulation parameters for the patient.

Typically, the stimulation parameters programmed into the neurostimulator can be adjusted by manipulating controls on an external control device to modify the electrical stimulation provided by the neurostimulator system to the patient. Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of movement disorders), while minimizing the volume of non-target tissue that is stimulated, which may results in side-effects. A typical stimulation parameter set may include the electrodes that are acting as anodes or cathodes, as well as the amplitude, duration, and rate of the stimulation pulses.

The large number of electrodes available, combined with the ability to generate a variety of complex stimulation pulses, presents a huge selection of stimulation parameter sets to the clinician or patient. To facilitate such selection, the clinician generally programs the external control device, and if applicable the neurostimulator, through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback and to subsequently program the external control device with the optimum stimulation parameters.

Despite the fact that a computerized programming system can be used to more efficiently program a neurostimulator, physicians and clinicians must still go through an extensive trial-and-error process to determine the stimulation parameter set or sets to be programmed into the neurostimulator. To address this concern, it is helpful to predict and display the size and location of the volume of tissue influenced by the stimulation provided the electrodes given a certain set of stimulation parameters (including electrode combination, pulse amplitude, pulse duration, and pulse frequency). For example, U.S. Pat. No. 7,346,382 describes a technique whereby a finite element model (FEM) of a defined candidate electrode morphology (which includes size, shape, and arrangement of electrodes) and surrounding tissue is solved for the second difference of the potential ($\Delta^2 V_e$), and then the volume of tissue likely to be affected (the "volume of activation" (VOA)) by various sets of stimulation parameters (pulse amplitude, pulse duration, and pulse frequency) is predicted.

While the VOA prediction technique described in U.S. Pat. No. 7,346,382 is advantageous, there are certain inherent disadvantages associated with modeling the stimulation leads. For example, a substantial amount of time and effort must be spent in developing FEM models for each new lead design, thereby presenting a bottleneck for lead development. For example, each FEM lead model must not only take into account the variability in electrode size and shape, but also the variability in electrode position due to, e.g., intra-lead electrode spacing, different lead configurations (e.g., a closely spaced side-by-side configuration, a closely spaced top-bottom configuration, a widely spaced top-bottom configuration, or a widely spaced side-by-side configuration), stagger of the leads, etc. Furthermore, because it is highly desirable that the implementation of the software package installed within each computerized programming system take into account all commercially available stimulation leads, computerized programming systems previously released into the field must be upgraded with new FEM lead models each time a new stimulation lead is designed.

There, thus, remains a need for an improved method and system for modeling stimulation leads.

SUMMARY OF THE INVENTION

In accordance with the present inventions, a system for a neurostimulation device is provided. The system comprises at least one processor configured for estimating at a plurality of spatial points a respective plurality of electrical field vectors resulting from a stimulation lead operating in accordance with the set of stimulation parameters. The processor(s) may optionally be configured for modeling the stimulation lead, and estimating the plurality of electrical field vectors based on the modeled stimulation lead. The system may optionally comprise telemetry circuitry, in which case, the processor(s) may be configured for programming the neurostimulation device with a set of stimulation parameters via the telemetry circuitry.

The processor(s) is further configured for determining an amplitude of each electrical field vector and an angle between each electrical field vector and a vector aligned with an axis of the stimulation lead, and estimating a tissue of volume activation about the stimulation lead based on the determined amplitude and angle of each electrical field vector. The system may further comprise a display device configured for displaying the tissue volume of activation to a user.

In one embodiment, the processor(s) may further be configured for determining the extent to which each electrical field vector acts as a cathode or an anode relative to the stimulation lead based on the angle between the respective electrical field vector and the vector aligned with the axis of the stimulation lead.

In another embodiment, the processor(s) is further configured for determining signs of a directional component and a positional component of each electrical field vector along a coordinate axis, and estimating the tissue volume of activation about the stimulation lead further based on the determined signs of the directional component and positional component of each electrical field vector relative to a coordinate axis perpendicular to the axis of the stimulation lead. For example, the system may further comprise memory storing a function having an amplitude, an angle, a sign of a directional component, and a sign of a positional component of an electrical field vector as an input, and an indicator of whether nerve tissue is activated at the position of the electrical field vector as an output, in which case, the processor(s) will be configured for estimating the tissue volume of activation based on the function. The processor(s) also be configured for determining whether the electrical field vector acts as a cathode or acts as an anode relative to the stimulation lead based on the signs of the directional component and positional component of each electrical field vector relative to the coordinate axis.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a spinal cord stimulator, pacemaker, a defibrillator, a cochlear stimulator, a retinal stimulator, a stimulator configured to produce coordinated limb movement, a cortical stimulator, peripheral nerve stimulator, microstimulator, or in any other neural stimulator configured to treat urinary incontinence, sleep apnea, shoulder sublaxation, headache, etc.

Figure 1:
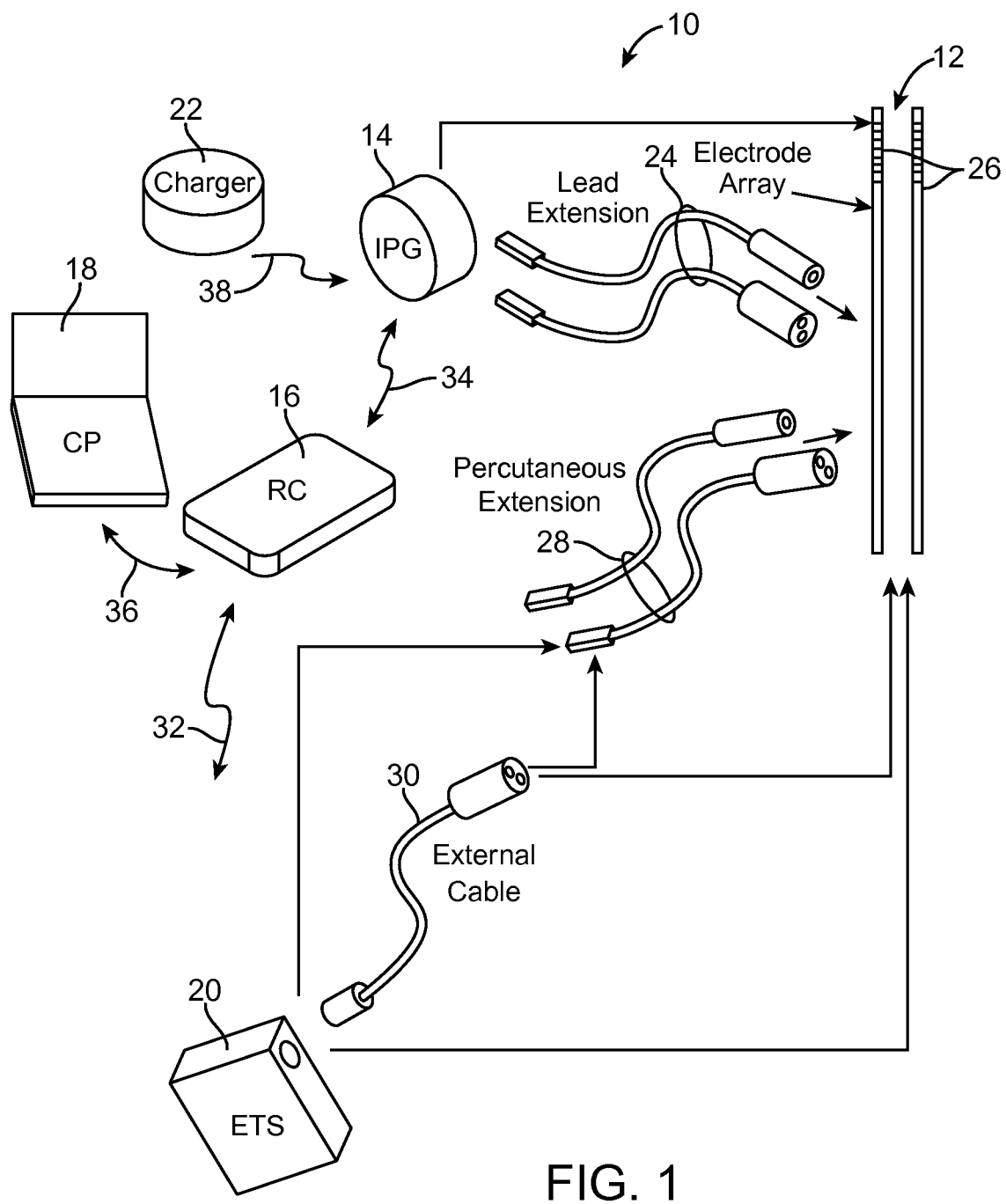
FIG. 1 is a plan view of an embodiment of a deep brain stimulation (DBS) system arranged in accordance with the present inventions.

Turning first to FIG. 1, an exemplary DBS neurostimulation system 10 generally includes at least one implantable stimulation lead 12 (in this case, two), a neurostimulator in the form of an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 may be arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
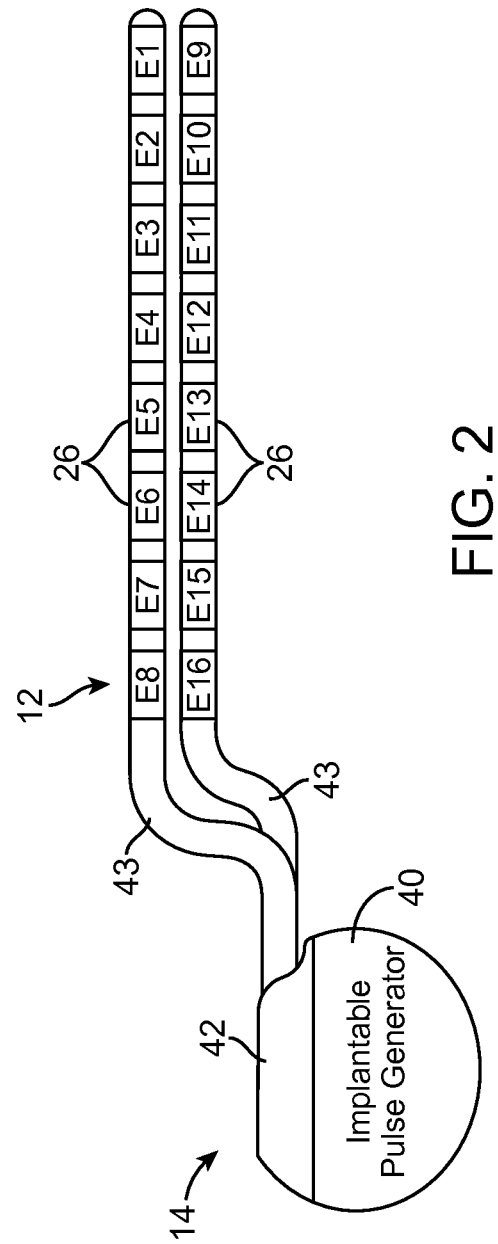
FIG. 2 is a profile view of an implantable pulse generator (IPG) and percutaneous leads used in the DBS system of FIG. 1.

Referring to FIG. 2, the IPG 14 comprises an outer case 40 for housing the electronic and other components (described in further detail below), and a connector 42 to which the proximal end of the stimulation lead 12 mates in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

Each of the stimulation leads 12 comprises an elongated cylindrical lead body 43, and the electrodes 26 take the form of ring electrodes mounted around the lead body 43. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 3:
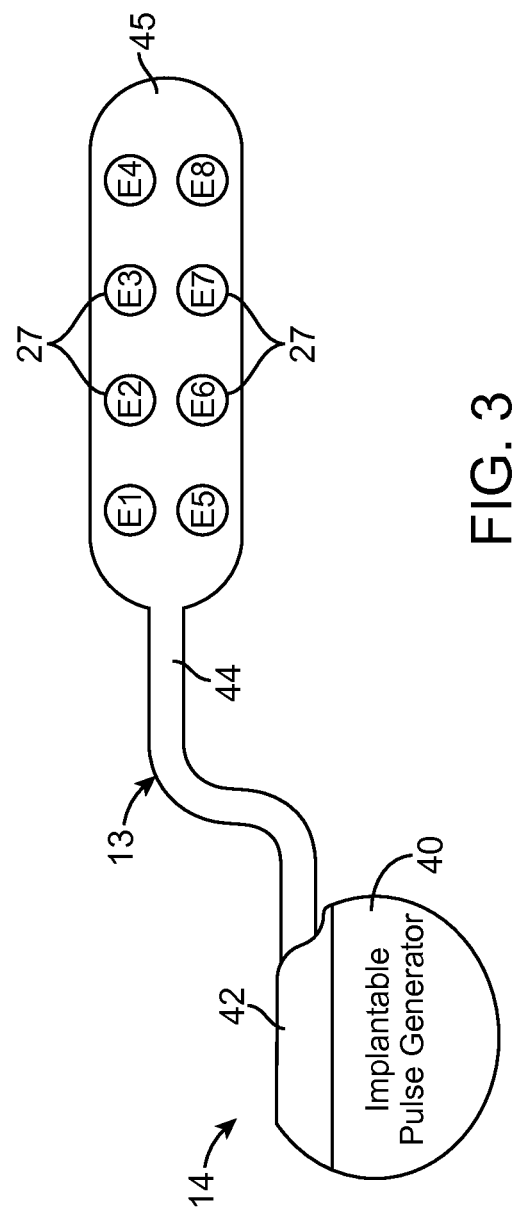
FIG. 3 is a profile view of an implantable pulse generator (IPG) and a surgical paddle lead that can be used in a cortical brain stimulation system similar to the DBS system of FIG. 1.

In an alternative embodiment illustrated in FIG. 3, a surgical paddle lead 13 can be used (e.g., if cortical brain stimulation is intended) instead of the percutaneous leads 12. The paddle lead 13 includes an elongated cylindrical lead body 44 and a distally-located paddle 45 with one side on which disk-shaped electrodes 27 (in this case, electrodes E1-E8) are carried. The electrodes 27 are arranged in a two-dimensional array in two columns along the axis of the stimulation lead 13. The actual number and arrangement of electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

As will be described in further detail below, the IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12(1) may be activated as an anode at the same time that electrode E11 on the second lead 12(1) is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

Figure 4:
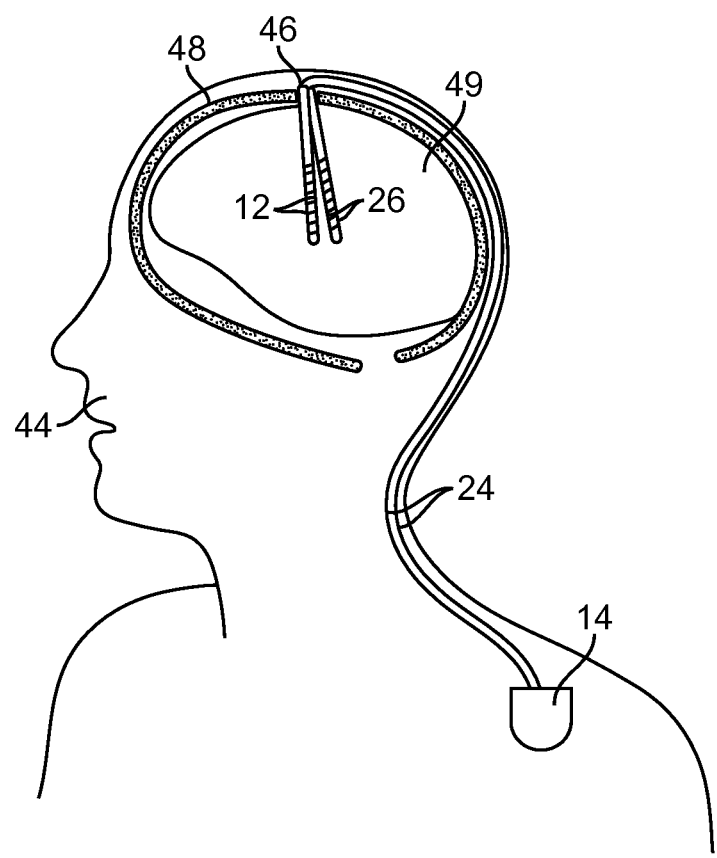
FIG. 4 is a plan view of the DBS system of FIG. 1 in use with a patient.

As shown in FIG. 4, two percutaneous stimulation leads 12 are introduced through a burr hole 46 (or alternatively, two respective burr holes) formed in the cranium 48 of a patient 44, and introduced into the parenchyma of the brain 49 of the patient 44 in a conventional manner, such that the electrodes 26 are adjacent a target tissue region, the stimulation of which will treat the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction. Due to the lack of space near the location where the stimulation leads 12(1) exit the burr hole 46, the IPG 14 is generally implanted in a surgically-made pocket either in the chest, or in the abdomen. The IPG 14 may, of course, also be implanted in other locations of the patient's body. The lead extension(s) 24 facilitates locating the IPG 14 away from the exit point of the stimulation leads 12(1).

Figure 5:
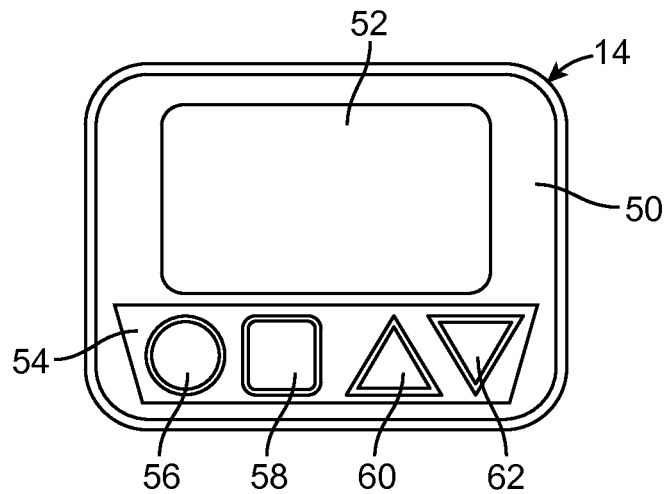
FIG. 5 is front view of a remote control (RC) used in the DBS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can actuated to increment or decrement any of stimulation parameters of the pulse generated by the IPG 14, including pulse amplitude, pulse width, and pulse rate. For example, the selection button 58 can be actuated to place the RC 16 in an "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 6:
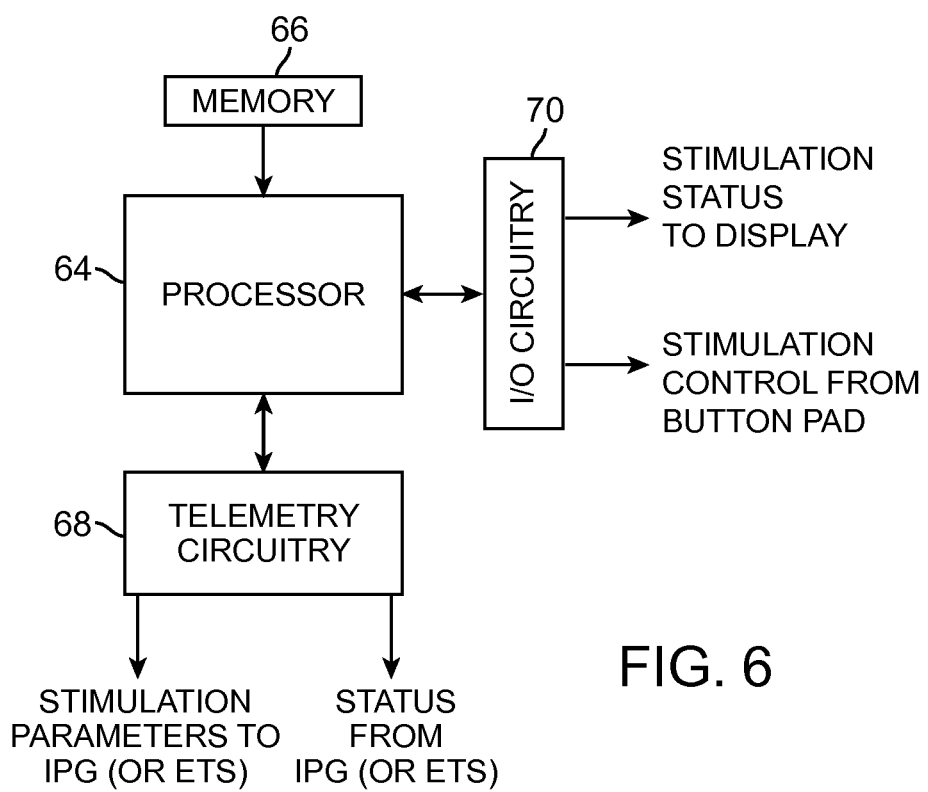
FIG. 6 is a block diagram of the internal components of the RC of FIG. 5.

Referring to FIG. 6, the internal components of an exemplary RC 16 will now be described. The RC 16 generally includes a processor 64 (e.g., a microcontroller), memory 66 that stores an operating program for execution by the processor 64, as well as stimulation parameter sets in a look-up table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 5). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 (or ETS 20) via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 in the brain.

The overall appearance of the CP 18 is that of a laptop personal computer (PC), and in fact, may be implanted using a PC that has been appropriately configured to include a directional-programming device and programmed to perform the functions described herein. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 (or ETS 20) to allow the optimum stimulation parameters to be determined based on patient response and feedback and for subsequently programming the IPG 14 (or ETS 20) with the optimum stimulation parameters.

Figure 7:
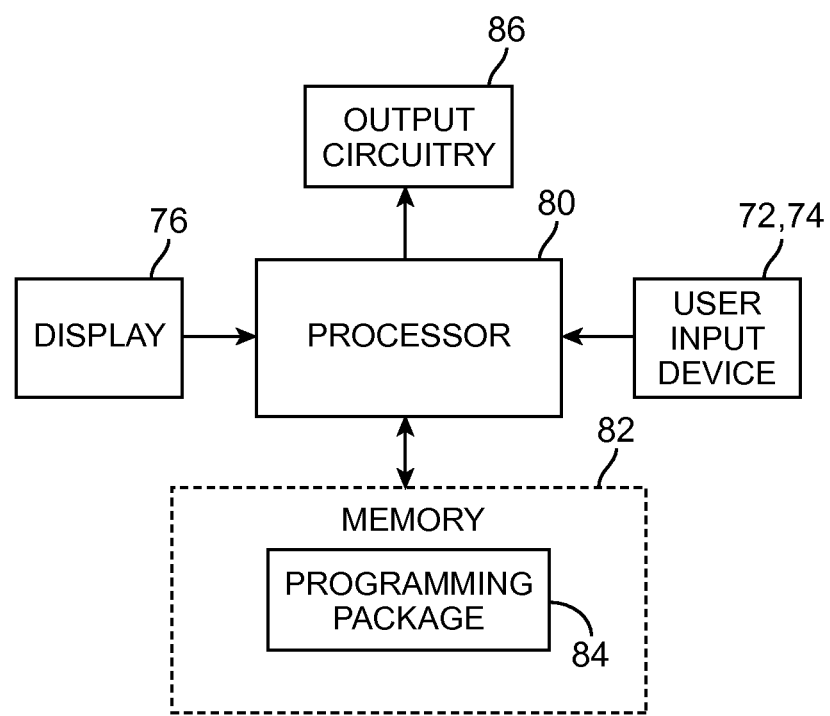
FIG. 7 is a block diagram of the internal components of a clinician's programmer (CP) used in the DBS system of FIG. 1.

To allow the clinician to perform these functions, the CP 18 includes a mouse 72, a keyboard 74, and a programming display screen 76 housed in a case 78. It is to be understood that in addition to, or in lieu of, the mouse 72, other directional programming devices may be used, such as a joystick, or directional keys included as part of the keys associated with the keyboard 74. As shown in FIG. 7, the CP 18 generally includes a processor 80 (e.g., a central processor unit (CPU)) and memory 82 that stores a stimulation programming package 84, which can be executed by the processor 80 to allow a clinician to program the IPG 14, and RC 16. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16, as well as obtaining status and measurement information from the IPG 14. Although the execution of the stimulation programming package 84 is described as being executed in the CP 18 to implement the navigation or programming paradigm, it should be appreciated that the programming package 84 may be executed in the RC 16 (although the processing power of the RC 16 may not be as great as that of the CP 18).

Significantly, in addition to providing conventional stimulation programming capability, the stimulation programming package 84 of the CP 18 can be executed to predict the volume of activation (VOA) for the tissue surrounding the implanted leads 12 given a set of stimulation parameters (including electrode combination, pulse amplitude, pulse duration, and pulse frequency). The VOA represents the neural region expected to typically be activated in response to the electrical stimulation. Conversely, tissue outside of the VOA are expected to typically remain unactivated in response to the electrical stimulation. In certain respects, the CP 18 predicts the tissue VOA in much the same manner as that described in U.S. Pat. No. 7,346,382; however, the CP 18 is capable of dynamically modeling an arbitrary electrode morphology (i.e., size, shape, and electrode spacing) input into the CP 18.

Figure 8:
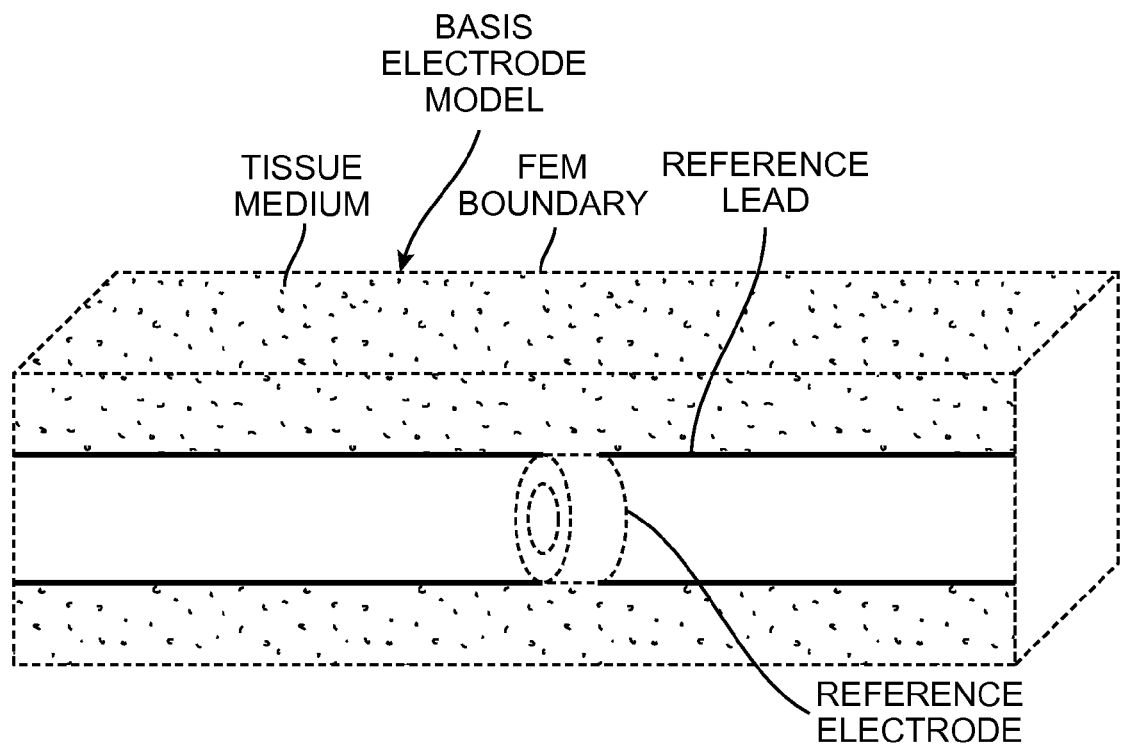
FIG. 8 is a perspective view of a basis electrode model used by the CP of FIG. 7 to construct a model of a selected electrode morphology input into the CP.
Figure 9:
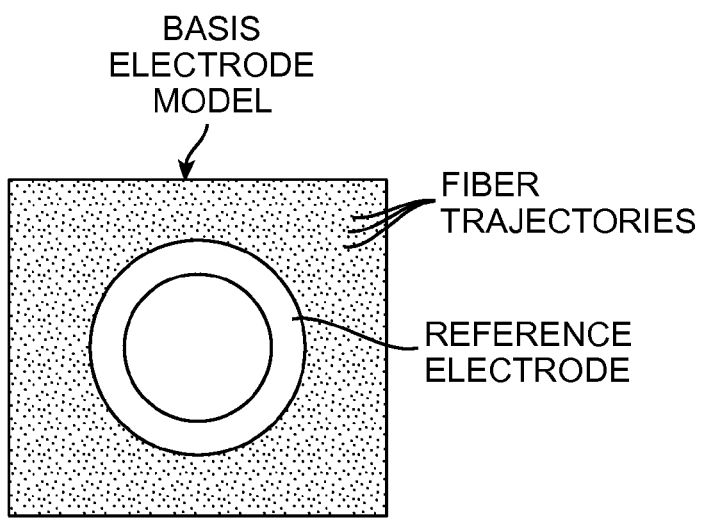
FIG. 9 is a cross-sectional view of a reference electrode used in the basis electrode model of FIG. 8.

The CP 18 accomplishes this by first building a model of the electrode morphology from a reference (basis) electrode model. That is, the reference electrode model is used as the basic building block for the entire electrode morphology. In the illustrated embodiment, the basis electrode model is a three-dimensional finite element model (FEM) of a ring electrode of the reference stimulation lead surrounded by a tissue medium of uniform conductivity (e.g., a uniform conductivity of 0.3 S/m), as illustrated in FIGS. 8 and 9. Because the ring electrode is outside of the insulative lead, the insulation of the lead body should not cover the ring electrode in the basis electrode model. However, the FEM may assume a sheath of encapsulation tissue surrounding the reference stimulation lead (e.g., having a thickness of 0.2 mm and a conductivity of 0.15 S/m). The boundary of the FEM model can be defined by a three-dimensional rectangle having a suitably sized length that is at least twice as great as the maximum span of the electrodes to be modeled. While the length of the rectangle is relatively large, the width and height (which in the illustrated embodiment are equal) need only be as large as the span of the stimulation effect of a single electrode. Although a three-dimensional rectangle is shown, any suitable three-dimensional shape, such as a cylinder, can be used. A commercially available software package, such as ANSYS 9.0 (Canonsburg, Pa.) can be used to implement the FEM. In alternative embodiments, rather than a FEM, the basis electrode model may be a boundary element model (BEM), or in its simplest form, an analytical model of a point source located in the uniformly conductive tissue medium by itself or located on an electrically insulative cylinder having the same diameter, or other dimensions as the lead.

Next, the basis electrode model is solved for a relevant electrical parameter that can be used to eventually determine the volume of the activated tissue surrounding the stimulation leads. For purposes that will described in further detail below, this electrical parameter is preferably spatially linear. For example, the electrical parameter may be a voltage, an activating function, an electrical field, a current-density, etc., is used. Furthermore, the electrical parameter may take the form of a scalar value (e.g., in the case of a voltage) or a vector having a set of directional values (e.g., in the case of an electrical field). As will also be described in detail below, the basis electrode model is preferably solved for an electrical field.

Next, a number of fiber trajectories within the boundary of the basis electrode model are determined (shown in FIG. 9 as extending perpendicular in and out of the page) For example, the fiber trajectories can be determined relative to the intended or desired orientation of the leads to be modeled. Such determination can be made based on the specific application or region of the patient where stimulation will ultimately occur For example, if axons of an approximate orientation with respect to the lead are anticipated for a certain application, data along trajectories of that orientation may chosen to be estimated with the model. Alternatively, a 3-dimensional grid of points can simply be defined within the boundary of the basis electrode model.

Next, the relevant electrical parameter information of the reference electrode model at a plurality of basis spatial points (e.g., selected points along the fiber trajectories (or alternatively, at the grid points)) is determined. This relevant electrical parameter information and corresponding basis spatial points can be stored in a look-up table (LUT) for a unit current amplitude at the reference point source, such that the electrical parameter information for any given basis spatial point can be obtained. This look-up table can be incorporated into the programming package 84 prior to installation within the memory of the CP 18. Thus, the CP 18 stores at least one solution for a basis electrode model that can be subsequently used to model solutions of any number of arbitrary electrode morphologies.

During operation in the field, one or more electrode morphologies can be entered into the CP 18. For example, the CP 18 can prompt the user to enter the number, size, and shape of electrodes for a new lead design. The CP 18 can then use the pre-stored basis electrode model to build a cumulative model for a selected electrode morphology that assumes a unit current on each of the electrodes).

Figure 10:
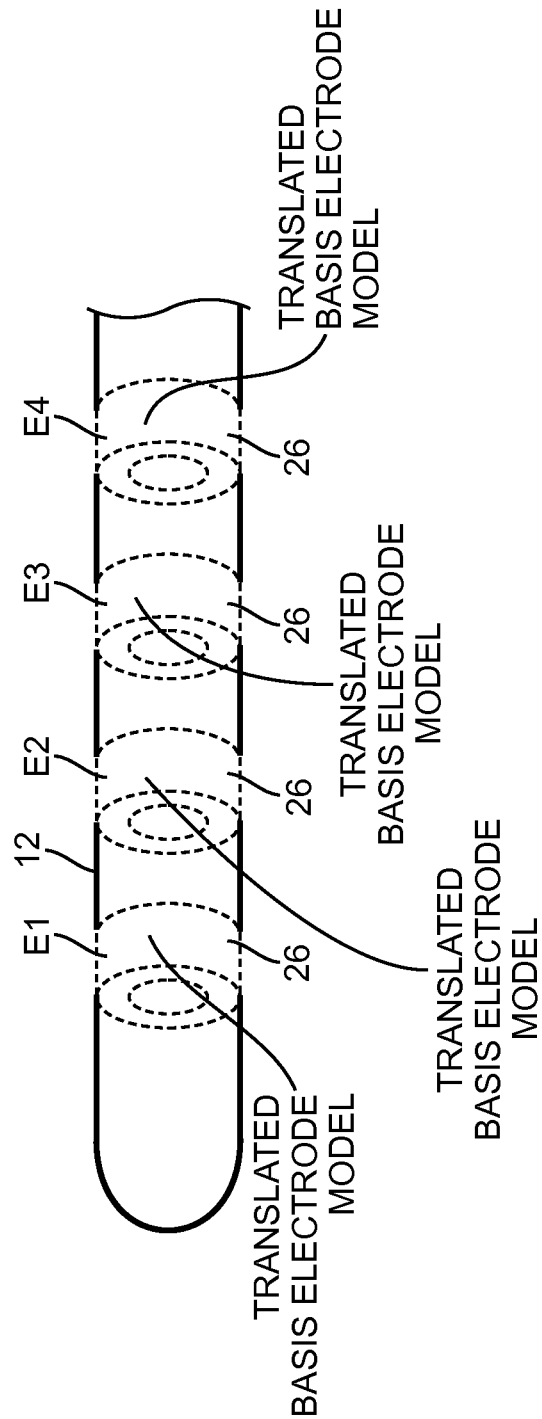
FIG. 10 is a perspective view of one exemplary electrode morphology that can be modeled using the basis electrode model of FIG. 8.

In particular, for each electrode of the selected electrode morphology to be modeled, the CP 18 obtains the basis electrode model solution (i.e., recalls the electrical parameter information from the LUT for each of the basis spatial points), and then spatially translates the basis electrode model at a selected resolution to each of the modeled electrodes a distance between the center of the basis electrode model and the center of the respective modeled electrode, as shown in FIG. 10.

In the illustrated embodiment, the CP 18 performs this step by deriving sets of electrical parameter information from the electrical parameter information of the basis electrode model, which derivation can be accomplished by duplicating the electrical parameter information of the basis electrode model. The derived electrical parameter information sets can then be spatially displaced relative to each other (via translation) to associate the derived electrical parameter information sets with the respective modeled electrodes.

Next, the CP 18 superposes the displaced electrical parameter information sets together. In the illustrated embodiment, the CP 18 performs this step by fitting the superposed electrical parameter sets to a common set of points (e.g., points along an m number of fiber trajectories or a three grid of points) surrounding the selected electrode morphology.

In one embodiment, the resolution of the basis spatial points is equal to the resolution of the common spatial points, and the resolution of the spatial translation of the basis electrode model is equal to the resolution of the common spatial points to ensure that electrical parameter information within each translated set is spatially registered with the common set of spatial points. In this case, the fitting of the translated electrical parameter information to the common set of points may be more computationally efficient. Alternatively, the resolution of the basis spatial points may not be equal to the resolution of the common spatial points and/or each basis electrode model may be translated the actual distance between the center of the basis electrode model and the center of the respective modeled electrode (i.e., resolution of translation is zero), and thus, the corresponding electrical parameter information of each displaced set may not be spatially registered with the common set of spatial points. In this case, the electrical parameter information can be fitted to the common set of spatial points via linear interpolation, which may be linear for purposes of computational efficiency.

After each electrode has been modeled using the foregoing technique, the superposed electrical parameter information for the modeled electrodes (which, in essence, is the cumulative model of the selected electrode morphology) can be stored, e.g., in a matrix having a first dimension that defines the specific common spatial point, and a second dimension that defines the specific modeled electrode, as will be discussed in further detail below. As discussed above, the electrical parameter information at each common spatial point can either be stored as a scalar value or a vector (set of directional values).

Figure 11:
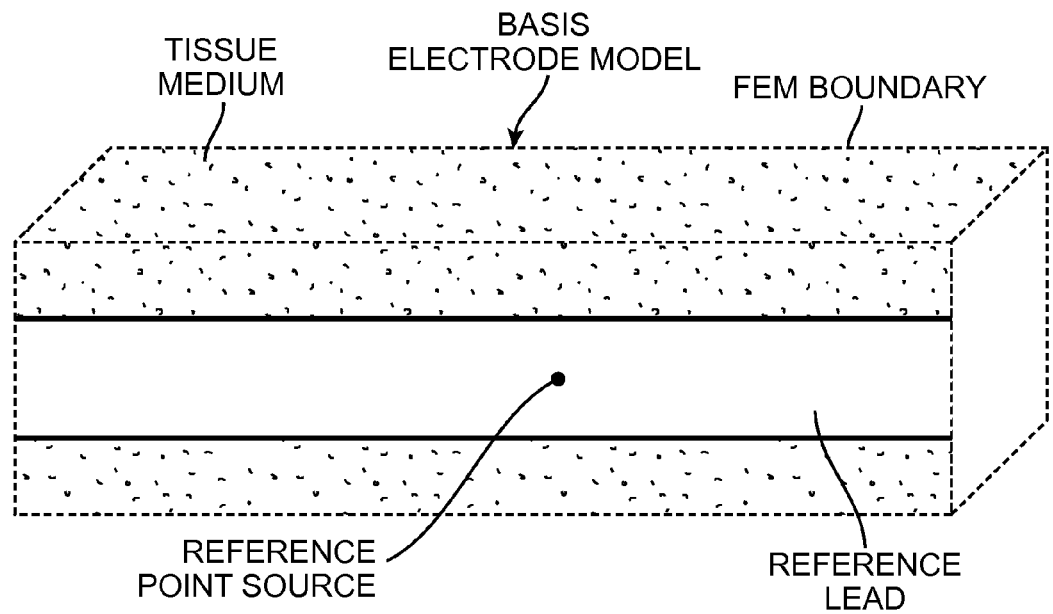
FIG. 11 is a perspective view of another basis electrode model used by the CP of FIG. 7 to construct a model of a selected electrode morphology input into the CP.

Although the basis electrode model has been described as only being used once for each electrode to be modeled (i.e., the electrical parameter information obtained from the LUT is only translated once for the modeled electrode), a basis electrode model can be used multiple times for each modeled electrode (i.e., the electrical parameter information obtained from the LUT are translated or otherwise moved multiple times for the modeled electrode), thereby enabling the use of generic basis models in providing an increased flexibility for modeling arbitrary electrode morphologies. In this case, the CP 18 generates the basis electrode model in the same manner as discussed above with respect to FIGS. 8 and 9, with the exception that, instead of modeling the entire ring electrode, an FEM is generated for a point source located on a surface of the reference stimulation lead, as illustrated in FIG. 11. In this case, the insulative body of the stimulation lead may be physically included within the model.

Figure 12:
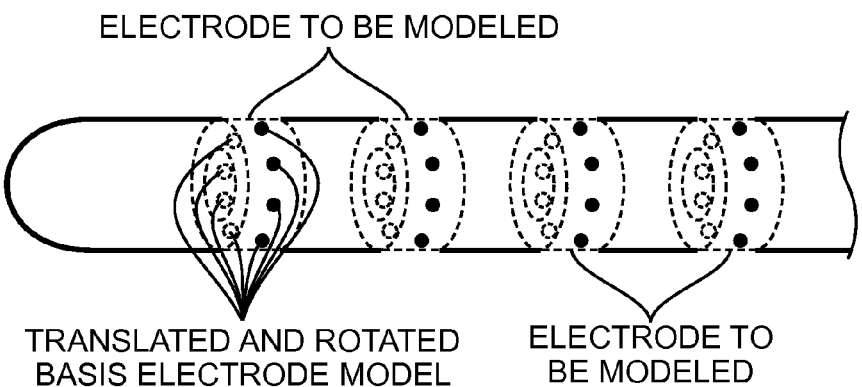
FIG. 12 is a perspective view of the exemplary electrode morphology of FIG. 10 that can be modeled using the basis electrode model of FIG. 11.

In particular, for each electrode of the selected electrode morphology to be modeled, the CP 18 obtains the basis electrode model solution (i.e., recalls the electrical parameter information from the LUT for each of the basis spatial points), and then both spatially translates the basis electrode model to the modeled electrode and rotating the basis electrode model about the modeled electrode several times (i.e., by translating and rotating electrical parameter sets derived (e.g., by duplication) from the electrical parameter information associated with the basis electrode model), as shown in FIG. 12. For example, the basis electrode model can be rotated about each electrode eight times (spaced 45 degrees apart) (four on front side of electrode shown in black, and four on back side of electrode shown in phantom). The translated and rotated electrical parameter information sets can then be superposed together by fitting the sets to a common set of points (e.g., points along an m number of fiber trajectories or a three grid of points) surrounding the selected electrode morphology in the same manner discussed above with respect to FIG. 10.

The CP 18 can then combine the superposed electrical parameter information sets for the electrode by scaling the electrical parameter information sets in inverse proportion of the number of basis electrode model rotations for each electrode (e.g., if the basis electrode model is rotated eight times, the electrical parameter information sets will be scaled down by ⅛). For example, if the electrical parameter information comprises scalar values, the electrical parameter values for the electrode may be added together at each spatial point. If the electrical parameter information comprises vectors, the electrical parameter vectors for the electrode may be added together at each spatial point.

Figure 13:
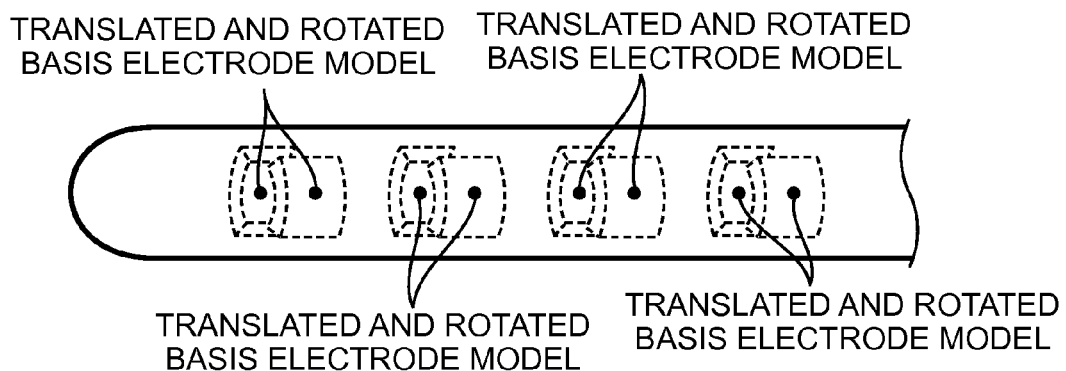
FIG. 13 is a perspective view of another exemplary electrode morphology that can be modeled using the basis electrode model of FIG. 11.

Although the electrode morphology illustrated in FIGS. 10 and 12 includes ring electrodes, it should be appreciated that electrode morphologies with other electrode shapes can be modeled using the basis electrode model. For example, FIG. 13 illustrates a stimulation lead with segmented electrodes (i.e., multiple arcuate electrodes are located at the same axial distance along the lead). In this case, after obtaining the electrical parameter information from the basis electrode model LUT (which in this case, it is based on a point source, although in other embodiments, can be generated by modeling the entirety of the segmented electrode in a similar manner described above with respect to FIG. 8), the CP 18 translates and rotates the basis electrode model (i.e., by translating and rotating electrical parameter sets derived (e.g., by duplication) from the electrical parameter information associated with the basis electrode model) to each of the segmented electrodes, as shown in FIG. 13, and then superposes the displaced electrical parameter sets in the same manner discussed above with respect to FIG. 10. Notably, the basis electrode model may be translated and/or rotated multiple times for each modeled electrode in a manner described above with respect to FIG. 12 to increase the accuracy of the modeled electrode morphology.

Figure 14:
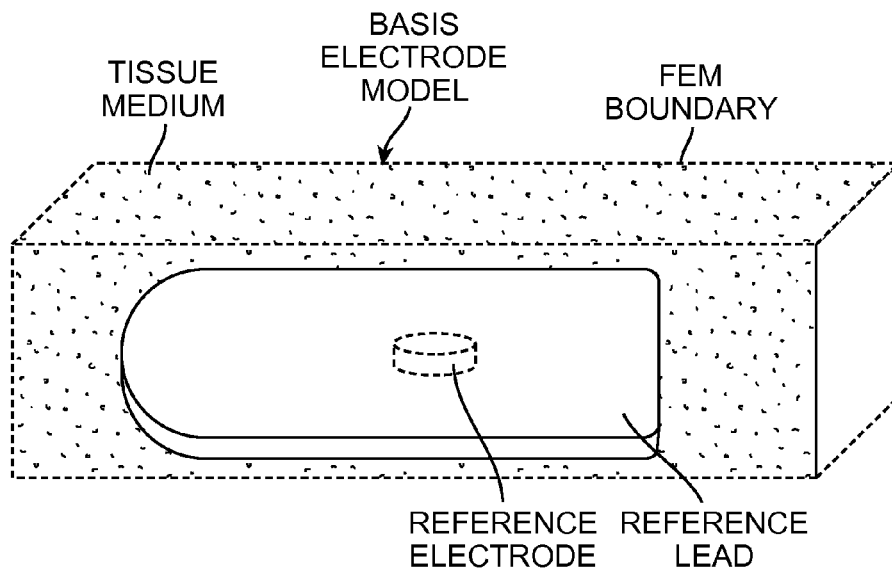
FIG. 14 is a perspective view of still another basis electrode model used by the CP of FIG. 7 to construct a model of a selected electrode morphology input into the CP.
Figure 15:
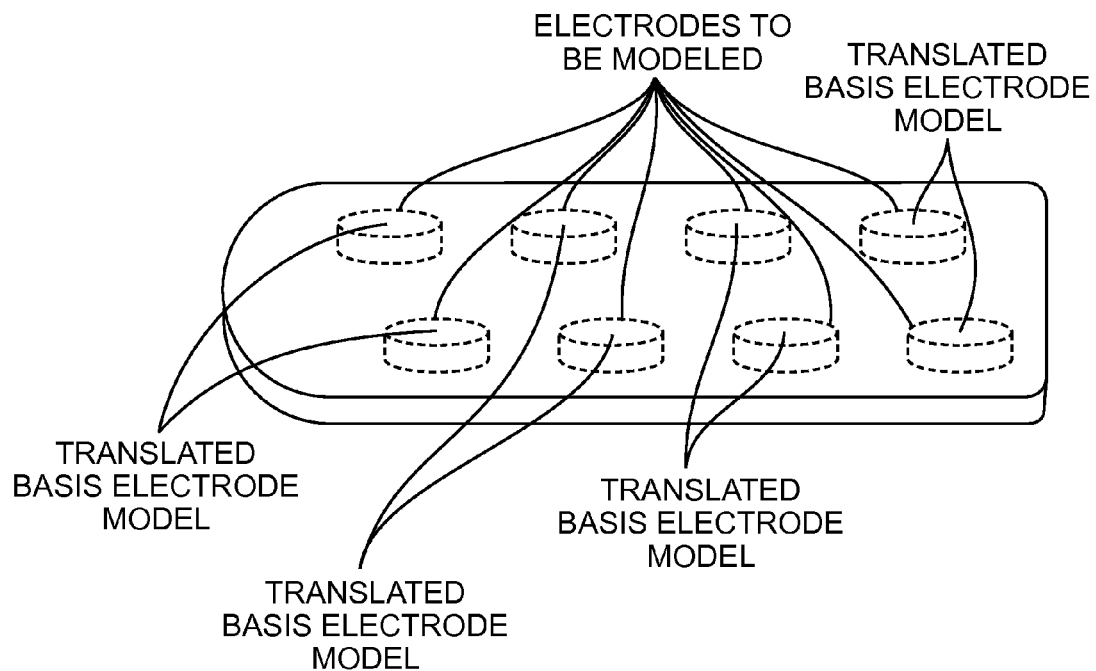
FIG. 15 is a perspective view of still another exemplary electrode morphology that can be modeled using the basis electrode model of FIG. 11.

Although modeled electrode morphologies have been described with respect to percutaneous leads (such as the stimulation lead 12 illustrated in FIG. 2), electrode morphologies related to surgical paddle leads (such as the surgical paddle lead 13 illustrated in FIG. 3) can be modeled. In this case, the CP 18 generates the basis electrode model in the same manner as discussed above with respect to FIGS. 8 and 9, with the exception that the insulative body will be planar and on one side of the electrodes, as shown in FIG. 14. The CP 18 then translates the basis electrode model (i.e., by translating electrical parameter sets derived (e.g., by duplication) from the electrical parameter information associated with the basis electrode model) to each of the electrodes, as shown in FIG. 15, and superposes the displaced electrical parameter sets in the same manner discussed above with respect to FIG. 10.

Figure 16:
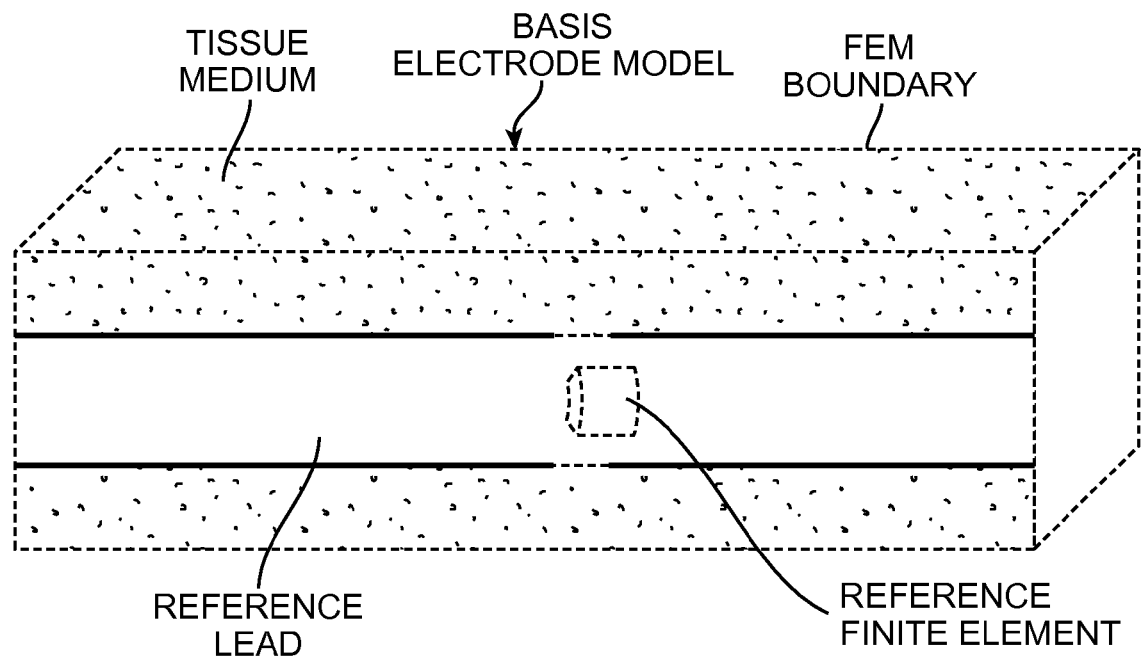
FIG. 16 is a perspective view of yet another basis electrode model used by the CP of FIG. 7 to construct a model of a selected electrode morphology input into the CP.
Figure 17:
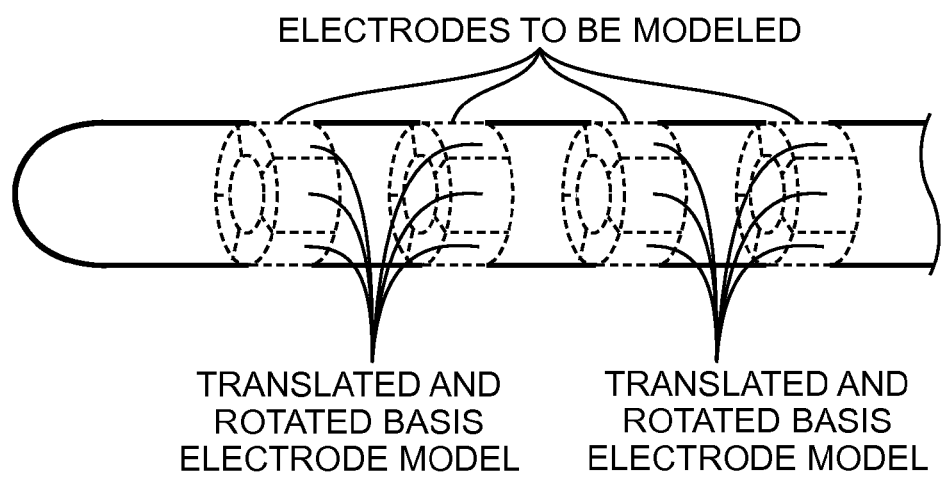
FIG. 17 is a perspective view of the exemplary electrode morphology of FIG. 10 that can be modeled using the basis electrode model of FIG. 16.

Notably, for cases where a point source is used to generate the basis electrode model, although the near-field FEM solution for this point source in a conductive tissue medium may differ from an actual near-field solution for a three-dimensional electrode in a conductive tissue medium, the difference between the far-field FEM solution for the point source in the conductive tissue medium and the far-field FEM solution for the three-dimensional electrode in the conductive tissue medium is insubstantial. Significantly, because the periphery of the volume of activation (VOA) will presumably be in the far-field, the accuracy of the FEM solution in the far-field will ultimately dictate the accuracy of the modeling techniques. Thus, the fact that the near-field FEM solution for the point source may differ from the near-field FEM solution for the three-dimensional electrode will be insignificant. Notwithstanding the foregoing, other types of sources besides point sources can be used as a reference FEM. For example, instead of a point source, an element with a finite area, such as a ring electrode segment, can be used, as shown in FIG. 16, and then spatially translated to each of the modeled electrodes to generate a cumulative model of the selected electrode morphology, as shown in FIG. 17.

It can be appreciated from the foregoing that each time a new lead type is released or otherwise designed, the lead type need only be input into the CP 18, which can then automatically generate a model of the lead type using the basis electrode model. Thus, only the database of the CP 18 will change with the addition of the new lead specification, and as such, the programming package 84 within the CP 18 need not have to be modified and recompiled. As such, the use of a basis electrode model to construct lead models is generalizable and computationally efficient. It should also be appreciated that, although only one basis electrode model has been described as being generated and stored, multiple basis electrodes can be generated and stored, and then selected by the CP 18 for modeling of a specific electrode morphology. For example, if a single electrode morphology includes two ring electrodes and six smaller segmented electrodes, two basis electrode models may be generated for a ring electrode and a segmented electrodes, and both used to model this electrode morphology.

Once the selected electrode morphology has been modeled (e.g., in any of the manners described above with respect to FIGS. 9-17), the CP 18 can then use the modeled electrode morphology to model an active electrode combination having associated electrical current values, which can be selected in a conventional manner either automatically or in response to a user input (e.g., via a manual user selection of electrodes and current values or via a current steering procedure). In particular, the CP 18 scales and/or changes the polarity of the electrical parameter information associated with each modeled electrode in accordance with the current value selected for the modeled electrode. The CP 18 combines the scaled electrical parameter information for each modeled electrode with each other. For example, if the electrical parameter information is a scalar value, the electrical parameter values for the respective active electrodes may be added together at each spatial point. If the electrical parameter information is a vector, the electrical parameter vectors for the respective active electrode may be added together at each spatial point.

The CP 18 can scale and/or change the polarity of the electrical parameter information associated with each modeled electrode in accordance with the current value selected for the modeled electrode, and combine the scaled electrical parameter information for each modeled electrode with each other by multiplying the electrode modeling matrix by a scaling vector.

Figure 18:
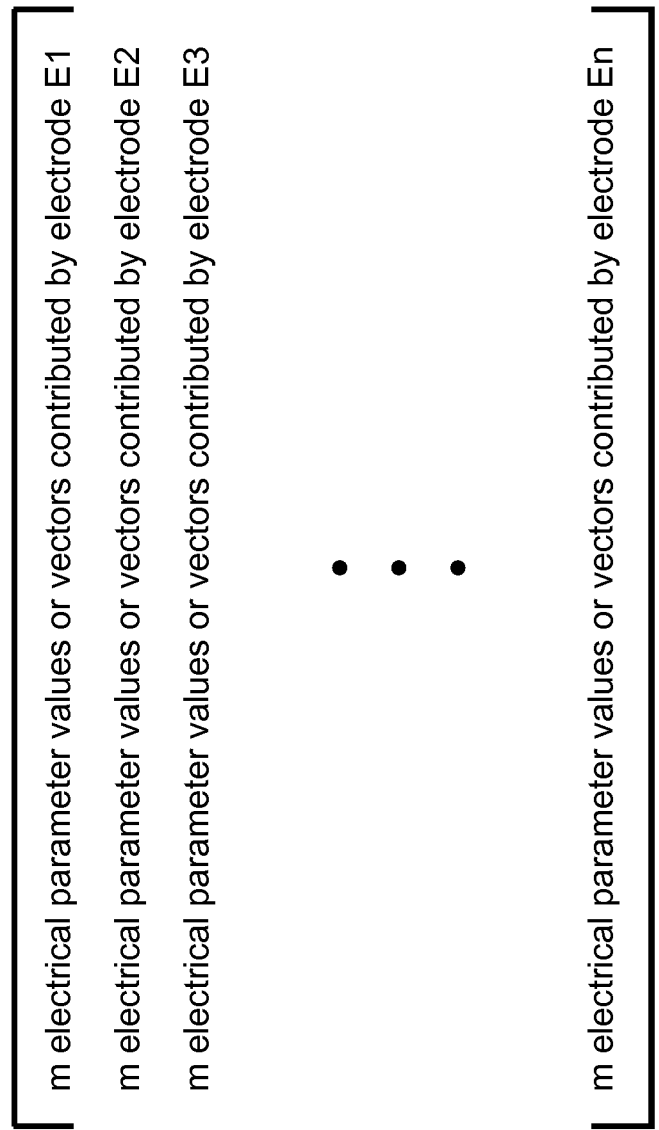
FIG. 18 is an electrode modeling matrix of electrical parameter information obtained from an exemplary electrode morphology.

As one example, consider an m×n electrode modeling matrix A illustrated in FIG. 18, where m is the number of spatial points at which the relevant electrical information is measured, and n is the number of electrodes in the electrode morphology. Assume that the reference point source is modeled with an anodic unit current, and anodic currents of 0.2 mA and 0.8 mA respectively flow through electrodes E4 and E5, cathodic currents of 0.4 and 0.6 mA respectively flow through electrodes E2 and E7, and all other electrodes are inactive. The electrode modeling matrix A can be multiplied by an n×1 scaling vector illustrated in FIG. 19 to obtain an m×1 vector containing electrical parameter values estimated at the spatial points.

Once the combination of active electrodes with the associated electrical current values has been modeled, the cumulative electrical parameter information (i.e., the electrical parameter information superimposed at each spatial point) is thresholded to determine the tissue VOA. In one advantageous embodiment, the electrical parameters are electrical field vectors. Significantly, the activation of any particular neuron is not only dependent on the amplitude of the stimulus, but the direction of the stimulus as well. Because an electrical field can be characterized by a vector (both amplitude and direction), electrical field vectors provide a convenient means for determining the activation of neural tissue. Other electrical parameter information can include activating functions, voltages, total net driving functions, etc.

Figures 19, 20:
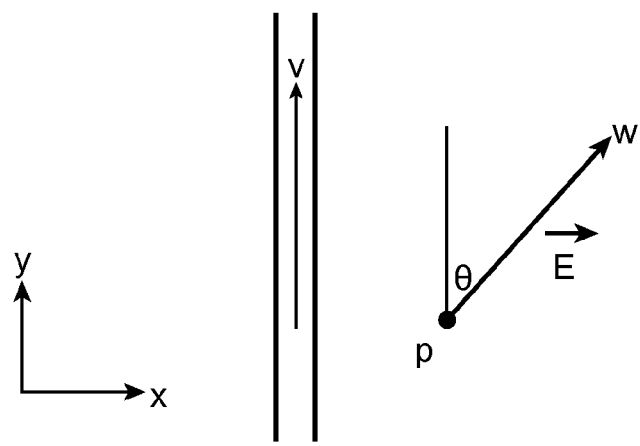
FIG. 19 is an exemplary technique for obtaining an electrical parameter vector that models an active electrode combination from the electrode modeling matrix of FIG. 18.
FIG. 20 is a plan view illustrating an electrical field vector estimated at an arbitrary point in space relative to a stimulation lead vector.

In particular, the "cathodeness" and "anodeness," along with the amplitude, of the electrical field at each spatial point along a particular nerve fiber can be analyzed to determine whether or not the nerve fiber will be activated. With reference to FIG. 20, a vector $\vec{v}$ representing an exemplary orientation of a stimulation lead and an exemplary vector $\vec{w}$ representing the orientation of an electrical field at an arbitrary point p is shown. The vectors $\vec{v}$ and $\vec{w}$ can be represented in a two-dimensional coordinate system (x,y) as:

$$\vec{v} = a\hat{i} + b\hat{j}$$

$$\vec{w} = c\hat{i} + d\hat{j},$$

where a, b, c, and d are constants, $\hat{i}$ is the directional component aligned with the x-axis, and $\hat{j}$ is the directional component aligned with the y-axis. It should be noted that although the vectors $\vec{v}$ and $\vec{w}$ are shown in a two-dimensional coordinate system, the vectors $\vec{v}$ and $\vec{w}$ may be characterized in a three-dimensional coordinate, in which case, they each will have a third directional component.

The "cathodeness" and "anodeness" of the electrical field at point p can be represented by the angle θ between the vectors $\vec{v}$ and $\vec{w}$, which can be determined as follows:

$$\cos\theta = \frac{v \cdot w}{|v||w|} = \frac{a \cdot c + b \cdot d}{\sqrt{a^2 + b^2} \cdot \sqrt{c^2 + d^2}}$$

If it is assumed that the lead is oriented along the y-axis of the coordinate system, and thus, a=0, b=1, then $$\cos\theta = \frac{d}{\sqrt{c^2 + d^2}}$$

It can be appreciated from FIG. 20 that as the angle θ approaches 90 degrees (away from the lead assuming the electrical field vector is located on the right side of the lead), the electrical field becomes more anodic relative to the lead, and as the angle θ approaches −90 degrees (towards the lead assuming the electrical field vector is located on the left side of the lead), the electrical field becomes more cathodic relative to the lead. However, because the solution to the above equation will always be positive, the sign of the angle θ will be lost (i.e., e.g., given the absolute values of c and d, it will not be known whether the angle θ is 90 degrees or −90 degrees). Thus, the degree to anode/cathode likeness, but not the "cathodeness" and "anodeness," of the electrical field can be determined from the absolute values c and d.

However, the sign of the directional value c and the sign of the position of the origin of the vector $\vec{w}$ (i.e., the point at which the electrical field is estimated) along the x-axis (designated the value x) can be examined to determine whether the electrical field is more like a cathode or more like an anode, with the magnitudes of the values c and d dictating the extent to which the electrical field acts as a cathode or an anode. For example, if the sign of the value x is positive (i.e., the origin of the vector is located on the right side of the lead), the electrical field at point p acts more like an anode if the sign of the value c is positive, and acts more like a cathode if the sign of the value c is negative. In contrast, if the sign of the value x is negative (i.e., the origin of the vector $\vec{w}$ is located on the left side of the lead), the electrical field at point p acts more like an cathode if the sign of the value c is positive, and acts more like an anode if the sign of the value c is negative.

A thresholding function of the angle θ (degree of cathodeness or anodeness of the electrical field) and the signs of the $\hat{i}$ directional component and x positional component of the electrical field (whether the electrical field acts as a cathode or an anode) at each point can thus be generated to determine the volume of activation (VOA) of the relevant tissue.

Figure 21:
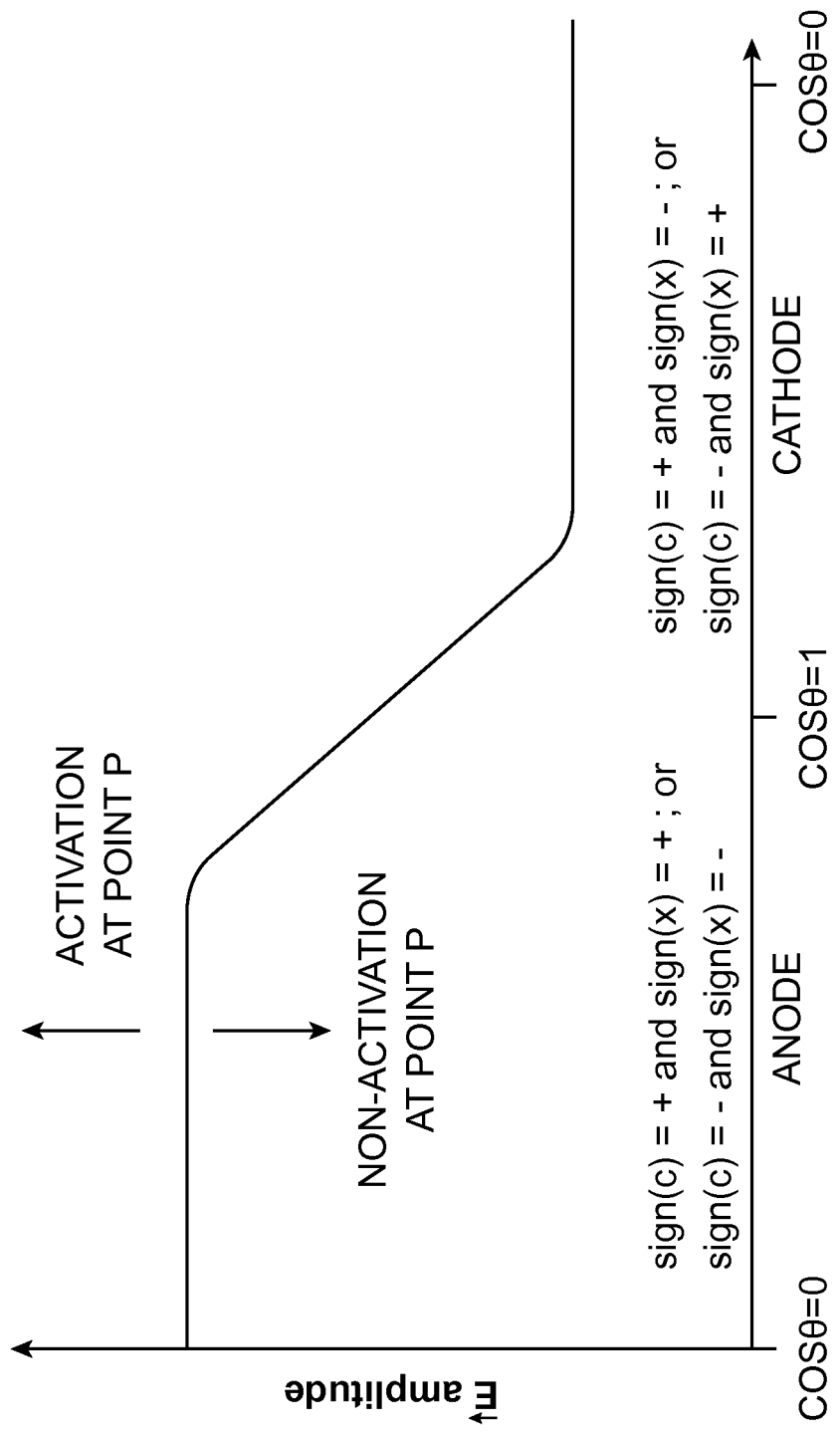
FIG. 21 is a plot illustrating an activation curve plotted as a function of the amplitude of the electrical field at an arbitrary point and the angle between the electrical field vector and stimulation lead vector of FIG. 20.

For example, referring to FIG. 21, a plot of an exemplary thresholding function is shown, with the y-axis of the plot representing the amplitude of the electrical field at an arbitrary point p and the x-axis of the plot representing the cosine of the angle θ. The area above the function curve is activated, whereas the area below the function curve is not activated. The shape and orientation of the function curve will ultimately depend on the directions of the nerve fibers relative to the lead. As shown in FIG. 21, an anodic electrical field (left side of the plot) requires a higher amplitude to activate nerve tissue at point p than a cathodic electrical field (right side of the plot), which would result from an assumption that the nerve fibers are oriented along the axis of the lead. The orientation of the fiber directions can be estimated from the specific application that the lead is being used in. For example, the nerve fiber orientation for spinal cord stimulation (SCS) applications may be different from the nerve fiber orientation for deep brain stimulation (DBS) applications. The offset of the function curve along the y-axis will not only depend on the amplitude of the electrical field, but the geometry of the pulse (both shape and duration) used to generate the electrical field. For example, the higher the pulse duration, the less amplitude is needed for the electrical field to activate the nerve tissue at the arbitrary point p. The threshold curve can be determined as a function of an electrical field input (both amplitude and direction) using a modeling analysis or using empirical data.

Thus, various function curves (e.g., a family of functions or a single surface or multi-dimensional function) that assume different pulse geometries and indications for stimulation can be pre-stored within the CP 18. The CP 18 will then be capable of determining whether nerve tissue at any given point p relative to the lead is activated, given the angle between the electrical field vector and the lead, and the $\hat{i}$ directional component and x positional component of the electrical field vector. Based on which points p in the tissue are expected to be activated, a representation of the VOA can then generated and displayed on the CP 18. The graphical representation of the VOA can be superimposed over or otherwise displayed with a graphical representation of the selected electrode morphology. Alternatively, the graphical representation of the VOA can be superimposed over an image of the anatomical region of interest.

By reviewing the graphical representation of the VOA, a user may determine whether the VOA representation properly coincides with the target anatomical region to be stimulated. If the VOA representation does not properly coincide with the anatomical region of interest (e.g., any portion of an anatomical region to be stimulated falls outside of the VOA representation, or any portion of an anatomical region not to be stimulated falls inside of the VOA representation), the stimulation parameters may be changed either manually by the user or automatically by the CP 18. In one embodiment, the CP 18 may generate and display a score indicating the extent to which the VOA representation coincides with the anatomical region of interest.

It should be appreciated that, although the processing functions disclosed above with respect to modeling of the electrode morphology, modeling an active electrode combination, and computing the VOA have been described as being performed in the CP 18, or alternatively, the RC 16, these processing functions, especially the real-time processing functions, such as the active electrode modeling and VOA computation, can be performed in the IPG 14. In this case, any data needed to display or otherwise convey information to a user can be telemetered from the IPG 14 to the CP 18 or RC 16.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A system for a neurostimulation device, comprising:
a user input device configured for receiving an electrode morphology having at least one electrode;
memory storing at least one basis electrode model;
at least one processor configured for modeling the at least one electrode by recalling the at least one basis electrode model from the memory, and using the recalled at least one basis electrode model multiple times to construct a model of the at least one electrode.

2. The control system of claim 1, wherein the at least one basis electrode model is used multiple times to construct the model of the at least one electrode by deriving a plurality of sets of spatially distributed electrical parameter information from the at least one recalled basis electrode model, and associating the derived electrical parameter information sets with different regions of the at least one electrode by spatially displacing the derived electrical parameter information sets relative to each other.

3. The control system of claim 2, wherein the at least one processor is configured for superposing the displaced electrical parameter information sets over each other, and combining the superposed electrical parameter information sets together to create a single electrical parameter information set.

4. The system of claim 3, wherein the at least one processor is configured for superposing the displaced electrical parameter information sets over each other by fitting the displaced electrical parameter information sets to a common set of spatial points.

5. The system of claim 4, wherein the at least one processor is configured for fitting the displaced electrical parameter information sets to the common set of spatial points by interpolating at least one of the displaced electrical parameter information sets.

6. The system of claim 4, wherein the at least one processor is configured for combining the superposed electrical parameter information sets together by summing the electrical parameter information sets at the common set of spatial points to create the single electrical parameter information set.

7. The system of claim 2, wherein the at least one electrode comprises a plurality of electrodes, and the derived electrical parameter information sets are respectively associated with the electrodes by respectively displacing the derived electrical parameter information sets at the respective electrodes.

8. The system of claim 7, wherein the at least one processor is configured for generating a stimulation parameter set comprising a plurality of electrical current amplitudes respectively for the plurality of electrodes, and for scaling the derived electrical parameter information sets in accordance with the relative electrical current amplitudes for the electrodes.

9. The system of claim 8, wherein the at least one processor is configured for combining the scaled electrical parameter information sets together to create a single electrical parameter information set.

10. The system of claim 7, wherein the at least one basis electrode model comprises a plurality of basis models.

11. The system of claim 2, wherein the at least one electrode comprises a single electrode, and the derived electrical parameter information sets are respectively associated with the single electrode by displacing the electrical parameter information sets at different regions of the single electrode.

12. The system of claim 2, wherein the derived electrical parameter information sets are spatially displaced relative to each other by translating electrical parameters relative to each other.

13. The system of claim 2, wherein the derived electrical parameter information sets are spatially displaced relative to each other by rotating electrical parameters relative to each other.

14. The system of claim 2, wherein each of the at least one basis electrode model comprises a set of electrical parameter information, and wherein the at least one processor is configured for deriving the electrical parameter information sets from the at least one recalled basis electrode model by duplicating the electrical parameter information set of the recalled basis electrode model.

15. The system of claim 2, wherein the electrical parameter information comprises electrical field vectors.

16. The system of claim 1, wherein the at least one processor is configured for generating a stimulation parameter set for the at least one electrode, and for estimating a tissue volume of activation about the at least one modeled electrode based on the stimulation parameter set.

17. The system of claim 16, further comprising a display device configured for displaying the tissue volume of activation to a user.

18. The system of claim 1, further comprising a telemetry circuitry, wherein the at least one processor is further configured for programming the neurostimulation device with a set of stimulation parameter information corresponding to the at least one electrode via the telemetry circuitry.

19. The system of claim 1, further comprising an external control device containing the user input device, the memory, and the at least one processor.

20. The system of claim 1, further comprising an implantable medical device containing at least a portion of the at least one processor.

* * * * *